United States Patent
Bernd et al.

(10) Patent No.: US 7,148,195 B2
(45) Date of Patent: Dec. 12, 2006

(54) LHRH ANTAGONISTS HAVING IMPROVED SOLUBILITY PROPERTIES

(75) Inventors: Michael Bernd, Frankfurt (DE); Bernhard Kutscher, Maintal (DE); Eckhard Gunther, Maintal (DE); Peter Romeis, Gelnhausen (DE); Thomas Reissmann, Frankfurt (DE); Thomas Beckers, Frankfurt (DE)

(73) Assignee: Zentaris GmbH, Frankfurt (DE)

( * ) Notice: Subject to any disclaimer, the term of this patent is extended or adjusted under 35 U.S.C. 154(b) by 304 days.

(21) Appl. No.: 10/671,573

(22) Filed: Sep. 29, 2003

(65) Prior Publication Data

US 2004/0266695 A1    Dec. 30, 2004

Related U.S. Application Data

(62) Division of application No. 09/525,007, filed on Mar. 14, 2000, now Pat. No. 6,627,609.

(51) Int. Cl.
*A61K 38/08* (2006.01)
*C07K 7/06* (2006.01)

(52) U.S. Cl. .......................... 514/15; 530/328

(58) Field of Classification Search ............... None
See application file for complete search history.

(56) References Cited

U.S. PATENT DOCUMENTS

| 4,581,169 A | 4/1986 | Nestor et al. |
| 4,628,044 A | 12/1986 | Loozen |
| 5,198,533 A | 3/1993 | Schally et al. |
| 5,300,492 A | 4/1994 | Haviv et al. |
| 5,527,777 A | 6/1996 | Thamm et al. |
| 5,942,493 A | 8/1999 | Kutscher et al. |

FOREIGN PATENT DOCUMENTS

| DE | 195 44 212 A1 | 6/1997 |
| EP | 0 328 090 A2 | 8/1989 |
| EP | 0 413 209 A1 | 2/1991 |
| EP | 0417454 | 3/1991 |
| WO | WO 97/19953 | 6/1997 |
| WO | WO 98/25642 | 6/1998 |
| WO | WO 00/55190 | 9/2000 |

OTHER PUBLICATIONS

Dermer 1994, Another Anniversary for the War on Cancer, Bio/Technology, vol. 12, p. 320.*
Haviv et al., "The Effect of NmeTyr$^5$ Substitution in Luteinizing Hormone-Releasing Hormone Antagonists", *J. Med. Chem.* 36(7), 928-933, 1993.

* cited by examiner

*Primary Examiner*—B. Dell Chism
(74) *Attorney, Agent, or Firm*—Pillsbury Winthrop Shaw Pittman LLP

(57) ABSTRACT

The invention relates to peptides which contain N-methylated amino acid units and have improved water solubility. Medicaments in which the peptides according to the invention are contained can be used for the treatment of hormone-dependent tumors and hormone-influenced non-malignant disorders.

4 Claims, No Drawings

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Glu His Trp Ser Tyr Gly Leu Arg Pro Gly
 1               5                  10
```

LHRH ANTAGONISTS HAVING IMPROVED SOLUBILITY PROPERTIES

CROSS REFERENCE TO RELATED APPLICATIONS

This is a divisional of U.S. patent application Ser. No. 09/525,007, filed Mar. 14, 2000, now U.S. Pat. No. 6,627,609 which in turn claims priority to German patent application no. 199 11 771.3, filed Mar. 17, 1999. Both applications are incorporated herein in their entirety by reference.

BACKGROUND OF THE INVENTION

1. Field of the Invention

The invention relates to LHRH antagonists having improved solubility properties, processes for the preparation of these compounds, medicaments in which these compounds are contained, and the use of the medicaments for the treatment of hormone-dependent tumours and hormone-influenced non-malignant disorders such as benign prostate hyperplasia (BPH) and endometriosis.

2. Background Information

The nomenclature used for the definition of the peptides agrees with that nomenclature explained by the IUPAC-IUB Commission on Biochemical Nomenclature (European J. Biochem. 1984, 138, 9–37), in which, in agreement with the conventional representation, the amino groups at the N terminus appear to the left and the carboxyl group at the C terminus appears to the right. The LH-RH antagonists such as the peptides according to the invention include naturally occurring and synthetic amino acids, the former including Ala, Val, Leu, Ile, Ser, Thr, Lys, Arg, Asp, Asn, Glu, Gln, Cys, Met, Phe, Tyr, Pro, Trp and His. The abbreviations for the individual amino acid residues are based on the trivial names of the amino acids and are Ala=alanine, Arg=arginine, Gly=glycine, Leu=leucine, Lys=lysine, Pal(3)=3-(3-pyridyl)alanine, Nal(2)=3-(2-naphthyl)-alanine, Phe=phenylalanine, Cpa=4-chlorophenylalanine, Pro=proline, Ser=serine, Thr=threonine, Trp=tryptophan, Try=tyrosine and Sar=sarcosine. All amino acids described here originate from the L series, if not mentioned otherwise. For example, D-Nal(2) is the abbreviation for 3-(2-naphthyl)-D-alanine and Ser is the abbreviation for L-serine. Substitutions on the ε amino group in the side chain of lysine are represented by a term placed in brackets behind Lys, if appropriate in the form of an abbreviation.

Other abbreviations used are:
Ac Acetyl
Atz 3-Amino-1,2,4-triazole-5-carbonyl
B 4-(4-Amidinophenyl)amino-1,4-dioxobutyl
Boc tert-Butyloxycarbonyl
Bop Benzotriazol-1-oxy-tris(dimethylamino)-phosphonium hexafluorophosphate
DCC Dicyclohexylcarbodiimide
DCM Dichloromethane
Ddz Dimethoxyphenyl-dimethylmethylenoxy-carbonyl (Dimethoxy-dimethyl-Z)
DIC Diisopropylcarbodiimide
DIPEA N,N-Diisopropylethylamine
DMF Dimethylformamide
Fmoc Fluorenylmethyloxycarbonyl
HF Hydrofluoric acid
HOBt 1-Hydroxybenzotriazole
HPLC High-pressure liquid chromatography
Me Methyl
TFA Trifluoroacetic acid
Z Benzyloxycarbonyl The peptides according to the invention are analogues of the luteinizing-hormone-releasing hormone (LH-RH), which has the following structure:

p-Glu-His-Trp-Ser-Tyr-Gly-Leu-Arg-Pro-Gly-NH$_2$ (SEQ ID NO:1), [LH-RH, gonadorelin].

For more than 20 years, researchers have sought selective potent antagonists of the LH-RH decapeptide [M. Karten and J. E. Rivier, Endocrine Reviews 7, 44–66 (1986)]. The high interest in such antagonists is based on their usefulness in the field of endocrinology, gynaecology, contraception and cancer. A large number of compounds have been prepared as potential LH-RH antagonists. The most interesting compounds which have been found to date are those compounds whose structures are a modification of the LH-RH structure.

The first series of potent antagonists was obtained by the introduction of aromatic amino acid residues into the positions 1, 2, 3 and 6 or 2, 3 and 6. The customary way of writing the compounds is as follows: the amino acids are first indicated which have taken the place of the amino acids originally present in the peptide chain of LH-RH, the positions in which the exchange took place being marked by superscripted figures. Furthermore, by the notation "LH-RH" placed afterwards it is expressed that these are LH-RH analogues in which the exchange has taken place.

Known antagonists are:
[Ac-D-Cpa$^{1,2}$, D-Trp$^{3,6}$] LH-RH (D. H. Coy et al., In: Gross, E. and Meienhofer, J. (Eds) Peptides; Proceedings of the 6th American Peptide Symposium, pp. 775–779, Pierce Chem. Co., Rockville III. (1979): [Ac-Pro$^1$, D-Cpa$^2$, D-Nal(2)$^{3,6}$] LH-RH (U.S. Pat. No. 4,419,347) and [Ac-Pro$^1$, D-Cpa$^2$, D-Trp$^{3,6}$] LH-RH (J. L. Pineda, et al., J. Clin. Endocrinol. Metab. 56, 420, 1983).

In order to improve the action of antagonists, basic amino acids, for example D-Arg, were later introduced into the 6 position. For example [Ac-D-Cpa$^{1,2}$, D-Trp$^3$, D-Arg$^6$, D-Ala$^{10}$] LH-RH(ORG-30276) (D. H. Coy, et al., Endocrinology 100, 1445, 1982); and
[Ac-D-Nal(2)1, D-Phe(4-F)$^2$, D-Trp$^3$, D-Arg$^6$] LH-RH (ORF 18260) (J. E. Rivier et al., in: Vickery B. H. Nestor, Jr. J. J., Hafez, E. S. E (Eds). LHRH and its Analogs, pp. 11–22 MTP Press, Lancaster, UK 1984).

Further potent LH-RH antagonists are described in WO 92/19651, WO 94/19370, WO 92/17025, WO 94/14841, WO 94/13313, U.S. Pat. No. 5,300,492, U.S. Pat. No. 5,140,009, EP 0 413 209 A1 and DE 195 44 212 A1.

The latter discloses compounds having a modified ornithine or lysine unit in position 6 and which correspond to the following formula:

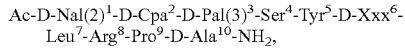

Ac-D-Nal(2)$^1$-D-Cpa$^2$-D-Pal(3)$^3$-Ser$^4$-Tyr$^5$-D-Xxx$^6$-Leu$^7$-Arg$^8$-Pro$^9$-D-Ala$^{10}$-NH$_2$, in which D-Xxx is an amino acid group of the general formula (VI)

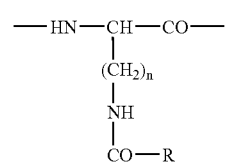

Further known LH-RH antagonists are antarelix, ganirelix and cetrorelix.

Antarelix:
Ac-D-Nal(2)$^1$-D-Cpa$^2$-D-Pal(3)$^3$-Ser$^4$-Tyr$^5$-D-Hci$^6$-Leu$^7$-Lys (iPr)$^8$-Pro$^9$-D-Ala$^{10}$-NH$_2$ Ganirelix:
Ac-D-Nal(2)$^1$-D-Cpa$^2$-D-Pal(3)$^3$-Ser$^4$-Tyr$^5$-D-hArg(Et)$_2$$^6$-Leu$^7$-hArg(Et)$_2$$^8$-Pro$^9$-D-Ala$^{10}$-NH$_2$ Cetrorelix:
Ac-D-Nal(2)$^1$-D-Cpa$^2$-D-Pal(3)$^3$-Ser$^4$-Tyr$^5$-D-Cit$^6$-Leu$^7$-Arg$^8$-Pro$^9$-D-Ala$^{10}$-NH$_2$.

SUMMARY OF THE INVENTION

The aim of the invention is to create novel LH-RH antagonists which have an increased enzymatic stability and significantly improved water solubility.

This object is achieved by compounds of the following general formula (I)

$$\text{A-Xxx}^1\text{-Xxx}^2\text{-Xxx}^3\text{-Xxx}^4\text{-Xxx}^5\text{-Xxx}^6\text{-Xxx}^7\text{-Xxx}^8\text{-Xxx}^9\text{-Xxx}^{10}\text{-NH}_2 \quad \text{(I)}$$

in which
A is an acetyl or a 3-(4-fluorophenyl)propionyl group,
Xxx$^1$ is D-Nal(1) or D-Nal(2),
Xxx$^2$-Xxx$^3$ is D-Cpa-D-Pal(3) or a single bond,
Xxx$^4$ is Ser,
Xxx$^5$ is N-Me-Tyr,
Xxx$^6$ is D-Cit, D-Hci or a D-amino acid group of the general formula (II)

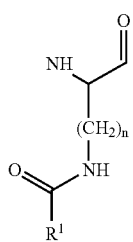

in which n is the number 3 or 4, where R$^1$ is a group having the general formula III $$-(CH_2)_p-CO-NR^2R^3 \quad \text{(III)}$$

where p is an integer from 1 to 4, R$^2$ is hydrogen or an alkyl group and R$^3$ is an unsubstituted or substituted aryl group or heteroaryl group, or R$^1$ is a 3-amino-1,2,4-triazole-5-carbonyl group or R$^1$ is a ring of the general formula (IV)

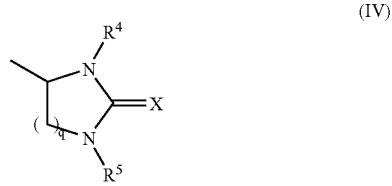

in which q is the number 1 or 2, R$^4$ is a hydrogen atom or an alkyl group, R$^5$ is a hydrogen atom or an alkyl group and X is an oxygen or sulphur atom,
Xxx$^7$ is Leu or Nle,
Xxx$^8$ is Arg or Lys(iPr),
Xxx$^9$ is Pro and
Xxx$^{10}$ is Ala, D-Ala or Sar, and their salts with pharmaceutically acceptable acids, in particular the acetates, embonates and trifluoroacetates.

Among the compounds according to the invention, those are particularly preferred in which Xxx$^6$ is D-[ε-N'-(imidazolidin-2-on-4-yl)formyl]-Lys, D-(3-amino-1,2,4-triazole-3-carbonyl)-Lys, abbreviated D-Lys(Atz) or D-[ε-N'-4-(4-Amidinophenyl)-amino-1,4-dioxo-butyl]-Lys, abbreviated D-Lys(B).

Further particularly preferred compounds according to the invention are:
Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-D-Ala$^{10}$-NH$_2$,
Ac-D-Nal(2)$^1$-D-Cpa$^2$-D-Pal(3)$^3$-Ser$^4$-N-Me-Tyr$^5$-D-Lys(Atz)$^6$-Leu$^7$-Arg$^8$-Pro$^9$-D-Ala$^{10}$-NH$_2$,
Ac-D-Nal(2)$^1$-D-Cpa$^2$-D-Pal (3)$^3$-Ser$^4$-N-Me-Tyr$^5$-D-Lys(B)$^6$-Leu$^7$-Lys(iPr)$^8$-Pro$^9$-D-Ala$^{10}$-NH$_2$,
Ac-D-Nal(2)$^1$-D-Cpa$^2$-D-Pal(3)$^3$-Ser$^4$-N-Me-Tyr$^5$-D-Lys(B)$^6$-Leu$^7$-Arg$^8$-Pro$^9$-D-Ala$^{10}$-NH$_2$,
Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-D-Ala$^{10}$-NH$_2$,
Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-Sar$^{10}$-NH$_2$,
Ac-D-Nal(2)$^1$-D-Cpa$^2$-D-Pal (3)$^3$-Ser$^4$-N-Me-Tyr$^5$-D-Hci$^6$-Nle$^7$-Arg$^8$-Pro$^9$-Sar$^{10}$-NH$_2$,
3-(4-Fluorophenyl) propionyl-D-Nal(1)$^1$-Ser$^4$-N-Me-Tyr$^5$-D-Lys(Atz)$^6$-Leu$^7$-Arg$^8$-Pro$^9$-D-Ala$^{10}$-NH$_2$,
Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-Sar$^{10}$-NH$_2$,
Ac-D-Nal(2)$_1$-D-Cpa$^2$-D-Pal(3)$^3$-Ser$^4$-N-Me-Tyr$^5$-D-Lys(B)$^6$-Nle$^7$-Arg$^8$-Pro$^9$-D-Ala$^{10}$-NH$_2$ and
Ac-D-Nal(2)$^1$-D-Cpa$^2$-D-Pal(3)$^3$-Ser$^4$-N-Me-Tyr$^5$-D-Lys(B)$^6$-Nle$^7$-Lys(iPr)$^8$-Pro$^9$-Sar$^{10}$-NH$_2$ and also their salts with the above-mentioned pharmaceutically acceptable acids.

The compounds according to the invention can be used for the treatment of hormone-dependent tumours, in particular prostate carcinoma or breast cancer, and also for non-malignant indications whose treatment necessitates LH-RH hormone suppression. For this, they are mixed with the customary vehicles and excipients and formulated as medicaments.

The synthesis of compounds according to formula (I) can both be carried out either by classical fragment condensation or by solid-phase synthesis according to Merrifield with synthesis following one another using D-lysine already acylated in the side chain with the carboxylic acid of the general formula R$^1$—COOH or by reaction of a decapeptide unit with the appropriate carboxylic acids by amide linkage in the side chain of D-lysine$^6$. Accordingly, the introduction of the R$^1$—CO-group can be performed in three different positions in the process: before the condensation of the individual units to give the peptide, after the incorporation of lysine or ornithine in the peptide chain, but before the condensation of the next unit or after condensation of all units.

The compounds of the formula (I) are synthesized according to the known methods, such as, for example, by pure solid-phase technique, partly solid-phase technique (so-called fragment condensation) or by the classical solution couplings (see M. Bodanszky, "Principles of Peptide Synthesis", Springer Verlag 1984).

For example, the methods of solid-phase synthesis are described in the textbook "Solid Phase Peptide Synthesis", J. M. Stewart and J. D. Young, Pierce Chem. Company, Rockford, III, 1984, and in G. Barany and R. B. Merrifield "The Peptides", Ch. 1, pp. 1–285, 1979, Academic Press Inc. Classical solution syntheses are described in detail in the treatment "Methoden der Organischen Chemie [Methods of Organic Chemistry] (Houben-Weyl), Synthese von Peptiden" [Synthesis of Peptides] E. Wünsch (Editor) 1974, Georg Thieme Verlag, Stuttgart, FRG.

The stepwise synthesis is carried out, for example, by first covalently bonding the carboxy-terminal amino acid whose α-amino group is protected to an insoluble support which is customary for this, removing the α-amino protective group of this amino acid, bonding the free amino group thus obtained to the next protected amino acid via its carboxyl group, and in this manner linking the customary amino acids of the peptide to be synthesized in the correct sequence step for step, and after linkage of all amino acids removing the finished peptide from the support and removing any further side function protective groups which may be present. The stepwise condensation is carried out in a conventional manner by synthesis from the corresponding, customarily protected amino acids.

The linkage of the individual amino acids to one another is carried out according to the methods customary for this; those particularly suitable are:

Symmetrical anhydride method in the presence of dicyclohexylcarbodiimide or diisopropylcarbodiimide (DCC, DIC)
Carbodiimide method generally
Carbodiimide/hydroxybenzotriazole method (see The Peptides, Volume 2, Ed. E. Gross and J. Meienhofer)

In the fragment coupling, the azide coupling, which proceeds without racemization, or the DCC-1-hydroxybenzotriazole or DCC-3-hydroxy-4-oxo-3,4-dihyro-1,2,3-benzotriazine method is preferably used. Activated esters of fragments can also be employed.

Esters of N-protected amino acids, such as, for example, N-hydroxysuccinimide esters or 2,4,5-trichlorophenyl esters, are particularly highly suitable for the stepwise condensation of amino acids. The aminolysis can be very well catalysed by N-hydroxy compounds which have approximately the acidity of acetic acid, such as, for example, 1-hydroxybenzotriazole.

Intermediate amino protective groups which present themselves are groups which are removed by hydrogenation, such as, for example, the benzyloxycarbonyl radical (=Z radical) or groups which can be removed by weak acid. Suitable protective groups for the α-amino groups are, for example: tertiary butyloxycarbonyl groups, fluorenylmethyloxycarbonyl groups, carbobenzoxy groups or carbobenzothio groups (if appropriate in each case having a p-bromo- or p-nitrobenzyl radical), the trifluoroacetyl group, the phthalyl radical, the o-nitrophenoxyacetyl group, the trityl group, the p-toluenesulphonyl group, the benzyl group, benzyl radicals substituted in the benzene nucleus (p-bromo- or p-nitrobenzyl radical) and the α-phenylethyl radical. Reference is also made here to P. Greenstein and Milton Winitz, Chemistry of Amino Acids, New York 1961, John Wiley and Sons, Inc., Volume 2, for example page 883 et seq., "Principles of Ppetide Synthesis", Springer Verlag 1984, "Solid Phase Peptide Synthesis", J. M. Stewart and J. D. Young, Pierce Chem. Company, Rockford, III, 1984, G. Barany and R. B. Merrifield "The Peptides", Ch. 1, pp. 1–285, 1979, Academic Press Inc., and also The Peptides, Volume 2, Ed. E. Gross and J. Maienhofer, Academic Press, New York. These protective groups are fundamentally also suitable for the protection of further functional side groups (OH groups, $NH_2$ groups) of the corresponding amino acids.

Hydroxyl groups present (serine, threonine) are preferably protected by benzyl groups and similar groups. Further amino groups not in the α-position (for example amino groups in the ω-position, guanidino group of arginine) are preferably orthogonally protected.

The individual amino acid units, excluding lysine or ornithine modified by the $R^1$—CO-group, are commercially obtainable. A possible course of the process for the preparation of the latter compounds is as follows:

1. The α-carboxylic acid group is amidated.
2. The ε-amino group is protected by the Z group.
3. The α-amino group is protected by the Boc group such that a selectivity with respect to the later removal of the amino protective groups results.
4. The Z group on the ε-amino group is removed.
5. The desired group $R^4$—Co— is introduced on the ε-amino group.
6. The Boc group on the α-amino group is removed.
7. The α-amino group is provided with the Z group.

For the introduction of the $R^1$—CO-group by reaction of the amino group of the lysine with appropriate carboxylic acid, suitable processes are fundamentally the same processes as described above for the linkage of the amino acids. However, condensation using carbodiimide, for example 1-ethyl-3-(3-dimethylaminopropyl)carbodiimide, and 1-hydroxybenzotriazole is particularly preferred.

The reaction for the linkage of the amino acids takes place in an inert solvent or suspending agent which is customary for this (for example dichloromethane), it being possible to add dimethylformamide, if necessary, to improve the solubility.

Suitable synthetic supports are insoluble polymers, for example polystyrene resin in bead form, which can be swollen in organic solvents (for example a copolymer of polystyrene and 1% divinylbenzene). The synthesis of a protected decapeptide amide on a methylbenzhydrylamine resin (MBHA resin, i.e. polystyrene resin provided with methylbenzhydrylamine groups), which affords the desired C-terminal amide function of the peptide after HF cleavage from the support, can be carried out according to the following flow diagram:

Flow Diagram

Peptide Synthesis Protocol

| Stage | Function | Solvent/Reagent (v/v) | Time |
|---|---|---|---|
| 1 | Washing | Methanol | 2 × 2 min |
| 2 | Washing | DCM | 3 × 3 min |
| 3 | Removal | DCM/TFA (1:1) | 1 × 30 min |
| 4 | Washing | Isopropanol | 2 × 2 min |
| 5 | Washing | Methanol | 2 × 2 min |
| 6 | Washing | DCM | 2 × 3 min |
| 7 | Neutralization | DCM/DIPEA (9:1) | 3 × 5 min |
| 8 | Washing | Methanol | 2 × 2 min |
| 9 | Washing | DCM | 3 × 3 min |
| 10 | STOP | Addition of the Boc-As in DCM + DIC + HOBt | |
| 11 | Coupling | DCM, optionally DCM/DCF | approx. 90 min |
| 12 | Washing | Methanol | 3 × 2 min |
| 13 | Washing | DCM | 2 × 3 min |

The Nα-Boc-protected amino acids are customarily coupled in a three fold molar excess in the presence of diisopropylcarbodiimide (DIC) and 1-hydroxybenzotriazole (HOBt) in CH$_2$Cl$_2$/DMF in the course of 90 min, and the Boc-protected group is removed by action of 50% trifluoroacetic acid (TFA) in CH$_2$Cl$_2$ for half an hour. To check for complete conversion, the chloranil test according to Christensen and the Kaiser's ninhydrin test can be used. Radicals of free amino functions are blocked by acetylation in a five fold excess of acetylimidazole in CH$_2$Cl$_2$. The sequence of the reaction steps of the peptide synthesis on the resin follows from the flow diagram. For the removal of the resin-bound peptides, the respective final product of the solid phase synthesis is dried in vacuo over P$_2$O$_5$ and treated at 0° C. for 60 min in a 500-fold excess of HF/anisole 10:1/v:v.

After distilling of HF and anisole in vacuo, the peptide amides are obtained as white solids by washing with anhydrous ethyl ether with stirring, and the removal of polymeric support additionally obtained is carried out by washing with 50% strength aqueous acetic acid. By careful concentration of the acetic acid solutions in vacuo, the respective peptides can be obtained as highly viscous oils, which are converted into white solids after addition of abs. ether in the cold.

Further purification is carried out by routine methods of preparative high-pressure liquid chromatography (HPLC).

The conversion of the peptides into their acid addition salts can be effected in a manner known per se by reaction thereof with acids. Conversely, free peptides can be obtained by reaction of their acid addition salts with bases. Peptide embonates can be prepared by reaction of trifluoroacetic acid salts (TFA salts) of the peptide with free embonic acid (pamoic acid) or the corresponding disodium salt of embonic acid. For this, the peptide TFA salt is treated in aqueous solution with the solution of disodium embonate in polar aprotic medium, preferably dimethylacetamide, and the pale yellow precipitate formed is isolated.

DETAILED DESCRIPTION OF THE INVENTION

The following examples serve to illustrate the invention without restricting it.

EXAMPLE 1

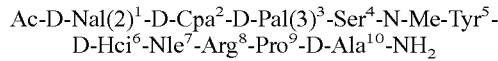

The synthesis was carried out according to a solid-phase flow diagram (Peptide Synthesis Protocol, p. 11) with DIC/HOBt coupling, starting from 3.3 g of MBHA resin (loading density 1.08 mmol/g). After HF cleavage from the polymeric support, 3.4 g of crude peptide were obtained, which were purified by standard processes of preparative HPLC. After subsequent freeze-drying, 1.43 g of HPLC-uniform product of the empirical formula C$_{72}$H$_{96}$N$_{17}$O$_{14}$Cl having correct FAB-MS: 1458.7 (M+H$^+$) (calc: 1457.7), and corresponding $^1$H-NMR spectrum were obtained.

$^1$H-NMR (500 MHz, D$_2$O/DMSO-d$_6$, δ in ppm): 8.7 to 7.2, several m, arom. H and incompletely exchanged NH; 6.92 and 6.58, 2d, 2×2H, arom. H p-Cl-Phe; 5.2 to 3.5, several m, Cα-H and aliph. H; 3.2 to 2.6, several m, aromat. Cβ-H 2.1 to 0.7, several m, residual aliphat. H; 1.70, s, 3H, acetyl; 1.20, d, 3H, Cβ-H Ala; 0.8, m, Cδ-H Leu

EXAMPLE 2

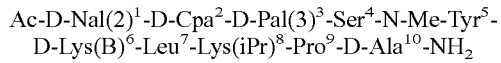

The synthesis was carried out according to a flow diagram (Peptide Synthesis Protocol, p. 11) with DIC/HOBt coupling, starting from 4.0 g of MBHA resin (loading density 1.11 mmol/g). After HF cleavage from the polymeric support, 4.87 g of crude peptide were obtained, which were purified by standard processes of preparative HPLC. After subsequent freeze-drying, 0.93 g of HPLC-uniform product was obtained, which was reacted with 4-amidinophenylamino-4-oxobutyric acid in the presence of BOP as a coupling reagent to give the desired compound. After fresh HPLC purification, 148 mg of target compound of the empirical formula C$_{85}$H$_{112}$N$_{17}$O$_{15}$—Cl having correct ESI-MS: 1647.6 (M+H$^+$) (calc: 1645.8), and corresponding $^1$H-NMR spectrum were obtained.

$^1$H-NMR (500 MHz, DMSO-d$_6$, δ in ppm):
10.4, s, 1H and 9.13, s, 2H, and 8.94, s, 2H, NHs of 4-amidinoaniline; 8.6 to 7.35, several m, arom. H and NH; 7.22 and 7.18, 2d, 4H, arom. H (pCl)Phe; 6.95 and 6.58, 2d, 4H, arom. H Tyr; 5.2 to 3.5, several m, Cα-H and aliphat. H; 3.3 to 2.4, several m, Cβ-H and N—CH$_3$; 2.1 to 1.1, several m, residual aliphat. H; 1.68, s, 3H, acetyl; 1.20, d, 3H, Cβ-H Ala; 0.83, dd, 6H, Cδ-H Leu

EXAMPLE 3

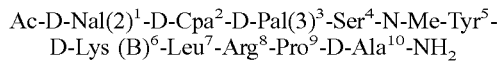

The synthesis was carried out according to a solid-phase flow diagram (Peptide Synthesis Protocol, p. 11) with DIC/HOBt coupling, starting from 4.0 g of MBHA resin (loading density 0.97 mmol/g). After HF cleavage from the polymeric support, 4.0 g of crude peptide were obtained, which were purified by standard processes of preparative HPLC. After subsequent freeze-drying, 1.39 g of HPLC-uniform product were obtained, which were reacted with 4-amidinophenylamino-4-oxobutyric acid in the presence of BOP as a coupling reagent to give the desired compound. After fresh HPLC purification, 440 mg of target compound of the empirical formula C$_{82}$H$_{106}$N$_{19}$O$_{15}$Cl having correct ESI-MS: 1632.7 (M+H$^+$) (calc: 1631.7), and corresponding $^1$H-NMR spectrum were obtained.

$^1$H-NMR (500 MHz, DMSO-d$_6$, δ in ppm):
10.4, s, 1H and 9.15, s, 2H, and 9.0, s, 2H, NHs of 4-amidinoaniline; 8.60, m, 2H, arom. H; 8.3 to 7.2, several m, arom. H and NH; 7.27 and 7.20, 2d, 4H, arom. H (pCl)Phe; 6.96 and 6.60, 2d, 4H, arom. H Tyr; 5.2 to 3.5, several m, Cα-H and aliphat. H; 3.2 to 2.4, several m, Cβ-H and N—CH$_3$; 2.1 to 1.1, several m, residual aliphat. H; 1.70, s, 3H, acetyl; 1.20, d, 3H, Cβ-H Ala; 0.85, dd, 6H, Cδ-H Leu

EXAMPLE 4

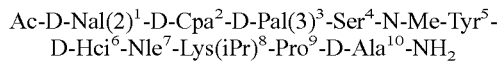

The synthesis was carried out according to a solid-phase flow diagram (Peptide Synthesis Protocol, p. 11) with DIC/HOBt coupling, starting from 2.5 g of MBHA resin (loading density 1.08 mmol/g). After HF cleavage from the polymeric support, 2.78 g of crude peptide were obtained, which were purified by standard processes of preparative HPLC. After subsequent freeze-drying, 400 mg of HPLC-uniform product of the empirical formula $C_{75}H_{102}N_{15}O_{14}Cl$ having correct ESI-MS: 1472.6 (M+H$^+$) (calc: 1471.7), and corresponding $^1$H-NMR spectrum were obtained.

$^1$H-NMR (500 MHz, D$_2$O/DMSO-d$_6$, δ in ppm):

8.62, m, 2H, 8.30, m, 2H, 7.80, m, 4H, 7.66, s, 1H, 7.47, m, 2H, 7.36, d, 1H, aromat. H; 7.25 and 7.20, 2 d, 4H, arom. H (pCl) Phe; 6.96 and 6.63, 2d, 4H, aromat. H Tyr; 5.10 to 4.0, several m, Cα-H and aliphat. H; 3.75 to 2.65, several m, Cβ-H and N-CH$_3$; 2.1 to 1.05, several m, residual aliphat. H; 1.74, s, 3H, acetyl; 1.23, d, 3H, Cβ-H Ala; 1.20, m, CH$_3$ isoprop.; 0.8, m, 3H, Cδ-H Nle

EXAMPLE 5

Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-Sar$^{10}$-NH$_2$

The synthesis was carried out according to a solid-phase flow diagram (Peptide Synthesis Protocol, p. 11) with DIC/HOBt coupling, starting from 2.5 g of MBRA resin (loading density 1.08 mmol/g). After HF cleavage from the polymeric support, 2.74 g of crude peptide were obtained, which were purified by standard processes of preparative HPLC. After subsequent freeze-drying, 840 mg of HPLC-uniform product of the empirical formula $C_{75}H_{102}N_{15}O_{14}Cl$ having correct ESI-MS: 1472.6 (M+H$^+$) (calc: 1471.7), and corresponding $^1$H-NMR spectrum were obtained.

$^1$H-NMR (500 MHz, D$_2$O/DMSO-d$_6$, δ in ppm):

8.6, m, 2H, 8.3, m, 2H, 7.85, m, 2H, 7.8, m, 2H, 7.65, s, 1H, 7.46, m, 2H, 7.35, d, 1H, aromat. H; 7.23 and 7.17, 2 d, 4H, arom. H (pCl)Phe; 7.0 and 6.6, 2d, 4H, aromat. H Tyr; 5.10 to 3.8, several m, Cα-H and aliphat. H; 3.75 to 2.6, several m, Cβ-H and N-CH$_3$; 2.2 to 1.05, several m, residual aliphat. H; 1.70, s, 3H, acetyl; 1.23, d, 3H, Cβ-H Ala; 1.20, m, CH$_3$ isoprop.; 0.8, m, 3H, Cδ-H Nle

EXAMPLE 6

3-(4-Fluorophenyl)propionyl-D-Nal(1)$^1$-Ser$^4$-N-Me-Tyr 5-D-Lys(Atz)$^6$-Leu$^7$-Arg$^8$-Pro$^9$-D-Ala$^{10}$-NH$_2$ The synthesis was carried out according to a solid-phase flow diagram (Peptide Synthesis Protocol, p. 11) with DIC/HOBt coupling, starting from 9.2 g of MBHA resin (loading density 1.08 mmol/g). After HF cleavage from the polymeric support, 5.8 g of crude peptide were obtained, which were purified by standard processes of preparative HPLC. After subsequent freeze-drying, 2.0 g of HPLC-uniform unsubstituted octapeptide were obtained, of which 0.4 mmol was reacted with 0.5 mmol of 3-amino-1,2,4-trizole-5-carboxylic acid in the presence of PyBOP as a coupling reagent to give 790 mg of crude product of the desired compound. After fresh HPLC purification, 200 mg of target compound of the empirical formula $C_{64}H_{86}N_{17}O_{12}F$ having correct FAB-MS: 1304.6 (M+H$^+$) (calc: 1303.6) were obtained.

$^1$H-NMR (500 MHz, D$_2$O/DMSO-d$_6$, δ in ppm):

8.14, m, 1H, 7.90, m, 1H, 7.80, m, 1H, 7.50, m, 2H, 7.35, m, 2H, 7.0, m, 6H, 7.63, m, 2H, aromat. H; 5.0, m, 1H, 4.83, m, 2H, 4.41, m, 1H, 4.30–4.05, several m, 4H, Cα-H; 3.66 to 2.25, several m, aliphat. and aromat. side-chain H; 2.95, s, and 2.75, s, N-Me; 2.05 to 1.1, several m, residual aliphat. H; 1.20, d, Cβ-H Ala; 0.75, m, 6H, Cδ-H Leu

EXAMPLE 7

Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-Sar$^{10}$-NH$_2$

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys (Boc)-OH, and the Fmoc protective groups were removed using 20% piperidine/DMF. After simultaneous removal of all side-chain protective groups and detachment from the polymeric support, the isolated crude peptide was purified by means of preparative HPLC. After freeze-drying, 98.5% pure decapeptide was obtained.

The substitution on the ε nitrogen of D-lysine with 4-(4-aminophenol)amino-1,4-dioxobutyric acid was carried out using PyBop in DMF with addition of DIPEA. The purification of the isolated crude peptide was carried out by means of preparative HPLC. The subsequent freeze-drying afforded about 99% pure product (trifluoroacetate) of the empirical formula C82H106ClN19O15 having correct FAB-MS of 1632 (M+H) (calc: 1631.78096)

EXAMPLE 8

Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-D-Ala$^{10}$-NH$_2$

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys (Boc)-OH, and the Fmoc protective groups were removed using 20% piperidine/DMF. After simultaneous removal of all side-chain protective groups and detachment from the polymeric support, the isolated crude peptide with a purity of about 71% (HPLC) was reacted further without purification.

The side-chain substitution of D-lysine with 4-(4-aminophenol)amino-1,4-dioxobutyric acid was carried out using PyBop in DMF with addition of DIPEA. The isolated crude peptide was purified by means of preparative HPLC. After subsequent freeze-drying, a 98.8% pure product (trifluoroacetate) of the empirical formula $C_{82}H_{106}ClN_{19}O_{15}$ having correct FAB-MS of 1632 (M+H) (calc: 1631.78096) was obtained.

EXAMPLE 9

Ac-D-Nal(2)$^1$-D-Cpa$^2$-D-Pal(3)$^3$-Ser$^4$-N-Me-Tyr$^5$-D-Lys(B)$^6$-Nle$^7$-Lys(iPr)$^8$-Pro$^9$-Sar$^{10}$-NH$_2$

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys (Boc)-OH, and the Fmoc protective groups were removed using 20% piperidine/DMF. After simultaneous removal of all side-chain protective groups and detachment from the polymeric support, the isolated crude peptide (concentration about 59%, HPLC) was purified by means of preparative HPLC. After freeze-drying, 95% pure decapeptide was obtained.

The side-chain substitution of D-lysine with 4-(4-aminophenol)amino-1,4-dioxobutyric acid was carried out using PyBop in DMF with addition of DIPEA. The isolated crude peptide was purified by means of preparative HPLC. After subsequent freeze-drying, a 96.6% pure product (trifluoroacetate) of the empirical formula $C_{85}H_{112}ClN17O_{15}$ having correct FAB-MS of 1646 (M+H) (calc: 1645.8218) was obtained.

The compounds according to formula I according to the invention were investigated for their receptor binding. The process closely followed the process described in Beckers et al., Eur. J. Biochem. 231, 535–543 (1995). Cetrorelix obtained according to the synthesis disclosed above was iodinated with [$^{125}$I] (Amersham; specific activity 80.5 Bq/fmol) using the IodoGen reagent (Pierce). The reaction mixture was purified by reverse-phase high-performance liquid chromatography, monoiodinated cetrorelix being obtained without unlabelled peptide. In each case, about 80% of the [$^{125}$I]-cetrorelix and the unlabelled compound according to the invention were suitable for the specific receptor association.

The compounds according to the invention can be tested for their in-vitro action using the following Methods 1 and 2, the binding affinities in the binding assay being determined with [$^{125}$I]-Cetrorelix (Method 1) and the functional activities being determined with triptorelin as an agonist stimulus (Method 2).

Method 1.

Receptor binding assay according to Beckers, T., Marheineke, K., Reiländer, H., Hilgard P. (1995) "Selection and characterization of mammalian cell lines with stable overexpression of human pituitary receptors for gonadoliberin (GnRH)" Eur. J. Biochem. 0.231, 535–543.

For investigation of the receptor binding, cetrorelix was iodinated using the IodoGen reagent (Pierce) with [$^{125}$I] (Amersham; 80.5 Bq/fmol specific activity). The reaction mixture was purified by high-performance liquid chromatography with exchanged phases, monoiodinated cetrorelix being obtained without unlabelled peptide. About 80% of the [$^{125}$I] cetrorelix was capable of specific receptor association.

The receptor binding assay was carried out under physiological conditions as described (Beckers et al., 1995) using intact cells. Subconfluent cultures of stably transfected LTK$^-$ cells, which express the human LHRH receptor, were separated off by incubation in NaCl/$P_i$ (137 mM NaCl, 2.7 mM KCl, 8.1 mM $Na_2HPO_4$, 11.47 mM $KH_2PO_4$)/1 mM EDTA and collected by centrifugation. The cell pellet was resuspended in binding buffer (DMEM without $H_2CO_3$, with 4.5 g/l of glucose, 10 mM Hepes pH 7.5, 0.5% (mass/volume) BSA, 1 g/l bacitracin, 0.1 g/l SBTI, 0.1% (mass/volume) $NaN_3$). For displacement assays, $0.25\times10^6$ cells/100 µl were incubated with approximately 225 pM of the [$^{125}$I]-cetrorelix (specific activity 5–10×10$^5$ dpm/pmol) and various concentrations of unlabelled compound according to the invention as competitor. The cell suspension in 100 µl of binding medium was layered in 400 µl assay tubes over 200 µl of 84% by volume silicone oil (Merck Type 550)/16% by volume paraffin oil. After incubation for 1 h at 37° C. with slow, continuous shaking, the cells were separated from the incubation medium by centrifugation for 2 min at 9000 rpm (rotor type HTA13.8; Heraeus Sepatec, Osterode/Germany). The tips of the tubes which contained the cell pellet were cut off. Cell pellet and supernatants were then analysed by counting the γ radiation. The amount of non-specifically bound material was determined at a final concentration of 1 µM with inclusion of unlabelled cetrorelix and was typically ≦10% of the total bound material. The analysis of the binding data was carried out using the EBDA/ligand analysis programme (Biosoft V3.0).

Method 2.

Functional Assay for the Determination of the Antagonistic Activity

The assay was carried out, provided with some modifications, as described in Beckers, T., Reiländer, H., Hilgard, P. (1997) "Characterization of gonadotropin-releasing hormone analogs based on a sensitive cellular luciferase reporter gene assay", Analyt. Biochem. 251, 17–23 (Beckers et al., 1997). 10,000 cells per well, which express the human LHRH receptor and a luciferase reporter gene, were cultured for 24 h in microtitre plates using DMEM with additives and 1% (v:v) FCS$_i$. The cells were then stimulated with 1 nM [D-Trp$^6$] LHRH for 6 h. Antagonistic compounds according to the invention were added before the stimulation and the cells were lysed at the end for the quantification of the cellular Luc activity. The calculation of the IC$_{50}$ values from dose-effect curves was carried out by non-linear regression analysis using the Hill model (Programme EDX 2.0 from C. Grunwald, Arzneimittelwerk Dresden).

The quantification of the Luc activity was carried out in duplicate essentially as described (Promega Technical Bulletins #101/161) using the respective luciferase assay system (Promega E4030). Owing to addition of coenzyme A (CoA), an oxidation of luciferyl-CoA takes place with advantageous kinetics. After the removal of the culture medium from the microtitre plate, the cells were lysed by addition of 100 µl of lysis buffer (25 mM tris-phosphate pH 7.8, 2 mM dithiothreitol, 2 mM 1,2-diaminocyclohexane-N,N,N',N'-tetraacetic acid (CDTA), 10% (v:v) glycerol, 1% (v:v) Triton X-100). After incubation at room temperature for 15 min, 10 µl of cell lysate were transferred into a white microtitre plate suitable for luminometric detection (Dynatech). The enzymatic reaction was initiated by addition of 50 µl of assay buffer (20 mM tricine pH 7.8, 1.07 mM $(MgCO_3)_4Mg(OH)_2$, 2.67 mM $MgSO_4$, 0.1 mM ethylenediaminetetraacetic acid (EDTA), 33.3 mM dithiothreitol, 270 µM coenzyme A, 470 µM glow-worm (Photinus pyralis) luciferin, 530 µM rATPNa$_2$). After one minute, the luminescence was determined for a total time of one second with a signal half-life of five minutes using the EG&G Berthold MicroLumat LB 96 P.

In this way, the following in-vitro data were obtained, K$_D$ being the binding affinities and IC$_{50}$ being the functional activity and pM being picomoles per liter:

| Compound | K$_D$ [pM] | IC$_{50}$ [pM] |
| --- | --- | --- |
| cetrorelix | 170 (21) | 198 (5) |
| Example 1 (Acetate salt) | n.d. | 242 (3) |
| Example 2 | 181 (1) | 684 (2) |
| Example 3 | 154 (1) | 492 (2) |
| Example 6 | n.d. | 221 (2) |
| Example 7 | n.d. | 1300 (1) |
| Example 8 | n.d. | 1400 (1) |
| Example 9 | n.d. | 4700 (1) | n.d. = not determined
( ) = number of independent experiments

The invention claimed is:

1. A compound of the general formula I $$\text{A-Xxx}^1\text{-Xxx}^2\text{-Xxx}^3\text{-Xxx}^4\text{-Xxx}^5\text{-Xxx}^6\text{-Xxx}^7\text{-Xxx}^8\text{-Xxx}^9\text{-Xxx}^{10}\text{-NH}_2 \quad (I)$$

in which:
A is an acetyl or a 3-(4-fluorophenyl)propionyl group,
$Xxx^1$ is D-Nal(1) or D-Nal(2),
$Xxx^2$-$Xxx^3$ is D-Cpa-D-Pal(3) or a single bond,
$Xxx^4$ is Ser,
$Xxx^5$ is N-Me-Tyr,
$Xxx^6$ is D-[ε-N'-(imidazolidin-2-on-4-yl)formyl]-Lys, D-(3-amino-1,2,4-triazole-3-carbonyl)-Lys, or D-[ε-N'-4-(4-amidino-phenyl)amino-1,4-dioxobutyl]-Lys,
$Xxx^7$ is Leu or Nle,
$Xxx^8$ is Arg or Lys(iPr),
$Xxx^9$ is Pro, and
$Xxx^{10}$ is Ala, D-Ala, or Sar,
and their salts with pharmaceutically acceptable acids.

2. The compound according to claim 1, wherein the salt is an acetate, trifluoroacetate, or embonate.

3. Method of treating prostate carcinoma or breast cancer comprising administering an effective amount of compound of the general formula I $$\text{A-Xxx}^1\text{-Xxx}^2\text{-Xxx}^3\text{-Xxx}^4\text{-Xxx}^5\text{-Xxx}^6\text{-Xxx}^7\text{-Xxx}^8\text{-Xxx}^9\text{-Xxx}^{10}\text{-NH}_2 \quad (I)$$

in which:
A is an acetyl or a 3-(4-fluorophenyl)propionyl group,
$Xxx^1$ is D-Nal(1) or D-Nal(2),
$Xxx^2$-$Xxx^3$ is D-Cpa-D-Pal(3) or a single bond,
$Xxx^4$ is Ser,
$Xxx^5$ is N-Me-Tyr,
$Xxx^6$ is D-[ε-N'-(imidazolidin-2-on-4-yl)formyl]-Lys, D-(3-amino-1,2,4-triazole-3-carbonyl)-Lys, or D-[ε-N'-4-(4-amidino-phenyl)amino-1,4-dioxobutyl]-Lys,
$Xxx^7$ is Leu or Nle,
$Xxx^8$ is Arg or Lys(iPr),
$Xxx^9$ is Pro, and
$Xxx^{10}$ is Ala, D-Ala, or Sar,
and their salts with pharmaceutically acceptable acids to an individual in need thereof.

4. Method of treating benign prostate hyperplasia or endometriosis comprising administering an effective amount of compound of the general formula I $$\text{A-Xxx}^1\text{-Xxx}^2\text{-Xxx}^3\text{-Xxx}^4\text{-Xxx}^5\text{-Xxx}^6\text{-Xxx}^7\text{-Xxx}^8\text{-Xxx}^9\text{-Xxx}^{10}\text{-NH}_2 \quad (I)$$

in which:
A is an acetyl or a 3-(4-fluorophenyl)propionyl group,
$Xxx^1$ is D-Nal(1) or D-Nal(2),
$Xxx^2$-$Xxx^3$ is D-Cpa-D-Pal(3) or a single bond,
$Xxx^4$ is Ser,
$Xxx^5$ is N-Me-Tyr,
$Xxx^6$ is D-[ε-N'-(imidazolidin-2-on-4-yl)formyl]-Lys, D-(3-amino-1,2,4-triazole-3-carbonyl)-Lys, or D-[ε-N'-4-(4-amidino-phenyl)amino-1,4-dioxobutyl]-Lys,
$Xxx^7$ is Leu or Nle,
$Xxx^8$ is Arg or Lys(iPr),
$Xxx^9$ is Pro, and
$Xxx^{10}$ is Ala, D-Ala, or Sar,
and their salts with pharmaceutically acceptable acids to an individual in need thereof.

* * * * *